United States Patent [19]

Esper et al.

[11] 4,268,468

[45] May 19, 1981

[54] METHOD OF MAKING A MEDICAL PROSTHESIS

[75] Inventors: Friedrich J. Esper, Leonberg; Hans-Martin Wiedenmann, Stuttgart, both of Fed. Rep. of Germany

[73] Assignee: Robert Bosch GmbH, Stuttgart, Fed. Rep. of Germany

[21] Appl. No.: 923,934

[22] Filed: Jul. 13, 1978

Related U.S. Application Data

[62] Division of Ser. No. 761,372, Jan. 21, 1977, abandoned.

[30] Foreign Application Priority Data

Jan. 21, 1977 [DE] Fed. Rep. of Germany ....... 2603456

[51] Int. Cl.³ .................... B29C 27/00; B29C 27/22; B29D 9/00; B29G 7/00
[52] U.S. Cl. .................................. 264/131; 264/137; 264/249; 264/255; 264/258; 264/274; 264/279; 264/299; 264/320; 156/245
[58] Field of Search ............... 128/92 C, 92 CA; 3/1.9–1.913; 264/1.9–1.913, 1; 156/245

[56] References Cited

U.S. PATENT DOCUMENTS

| | | | |
|---|---|---|---|
| 3,177,278 | 4/1965 | Schilling | 264/250 |
| 3,555,136 | 1/1971 | Rouault | 264/126 |
| 3,662,405 | 5/1972 | Bortz et al. | 3/1.9 |
| 3,683,422 | 8/1972 | Stemmer et al. | 3/1.9 |
| 3,847,888 | 11/1974 | Baumgaertner | 264/126 |
| 3,867,728 | 2/1975 | Stubstad et al. | 3/1.91 |
| 3,893,196 | 7/1975 | Hochman | 3/1.913 |
| 3,938,198 | 2/1976 | Kahn et al. | 128/92 CA |
| 3,986,212 | 10/1976 | Sauer | 3/1.912 |
| 3,992,725 | 11/1976 | Homsey | 128/92 C |
| 4,055,862 | 11/1977 | Farling | 128/92 C |
| 4,127,902 | 12/1978 | Homsy | 128/92 C |

*Primary Examiner*—W. E. Hoag
*Attorney, Agent, or Firm*—Frishauf, Holtz, Goodman & Woodward

[57] ABSTRACT

A bone replacement, for example a portion of a hip joint, a bone junction plate, or the like, includes a core element of a fiber-reinforced thermosetting material with a surface element made of a biologically compatible material, typically polyethylene, completely surrounding the core element. The outside surface element is internally interlocked with the core element, by being molded in one heat treatment operation which simultaneously cures the thermosetting material while molding the outside biologically compatible surface element thereto and interlocking and integrating the two elements into one unitary structure. Preferably, the fiber reinforcement is formed as fibers, woven mats, felted mats, or the like, and the surface element may, likewise, include a reinforcement beneath the surface actually in contact with the human body.

10 Claims, 4 Drawing Figures

METHOD OF MAKING A MEDICAL PROSTHESIS

This is a division, of application Ser. No. 761,372, filed Jan. 21, 1977 now abandoned.

The present invention relates to a method of making a prosthetic structure or appliance for medical use, for example as replacement or for repair of human or animal bones in the living body.

It has previously been proposed to replace bones in the living body for example to replace human bones for the hip joint, by means of metal alloys or aluminum oxide ceramic elements, as well as by combinations of such materials. It has also been proposed to utilize combined metal-plastic systems and to make such prosthetic units of carbon or graphite. Furthermore, it has been proposed to utilize reinforcements and connecting plates for bones to facilitate setting of bones after fractures by using metallic plates or metal alloys.

The materials heretofore used all have some disadvantages. Replacement of a bone in a hip joint usually involves replacement of the femur. The replacement bone is practically always made of a metallic material. The ball joint portion of the hip joint is also almost exclusively made of metal, usually of a metal alloy. Recently, it has been proposed to make the ball portion of aluminum oxide. The socket for the hip joint is also frequently made of plastics, although aluminum oxide, or combinations of aluminum oxide and plastics have been proposed.

Some type of bone cement or adhesive is used to secure the shaft of the femur, or the socket, respectively, to the still existing bone fragments. Bone cement does deteriorate in the course of time, and it has been found that the implanted elements become loose. Newer attachment and connecting techniques also did not result in complete assurance of long-term, reliable connection. It is believed that the difficulties result primarily in the substantial difference in the modulus of elasticity between bones and implanted elements. The high modulus of elasticity of the implanting material is disadvantageous since it does not dampen impacts or jars as bones do, but rather transfers any shocks without damping directly to the body. Corrosion problems have not been completely solved when using metal alloys. Additionally, some metal alloys are subject to wear. Aluminum oxide is subject to wear and, further, is sensitive to impact and shock.

Connecting or bracing elements used in the treatment of fractures also have disadvantages if plates with a high elasticity modulus are applied. Metal plates are used to fix bone fragments and ends separated by a fracture. These plates are stiff and cannot be readily applied to the actual shape of the bone. In certain instances, high loading peaks occur at the ends of the connecting plates, which may result in secondary fractures. The large difference in the modulus of elasticity between plates and bones can also lead to softening of the bones, that is, spongiosis, which again may result in secondary fractures.

Pure plastic materials have not been used, since their strength regarding tension, torsion, resistance to bending, and resistance to repeated change in bending direction is insufficient to permit their application for medical prosthetic uses.

It is an object of the present invention to provide a method to make an prosthetic appliance, for use in medicine, which has physical and mechanical properties matching those of the bones as closely as possible and which, additionally, is stable with respect to the biological environment in which it is placed and compatible therewith.

SUBJECT MATTER OF THE PRESENT INVENTION

Briefly, the prosthetic appliance is made by forming a composite material having a core element which is made of a fiber structure soaked in thermosetting plastic as the carrying element, surrounded by a fiber surface element and an outer a material which is biologically compatible with the human body, or the body in which the appliance is to be inserted. The soaked core element and the surface element are molded and cured in a heated compression mold. The surface element which is biologically compatible can also be reinforced by fibers and, preferably, may include a fiber-reinforced thermoplastic material.

Thermoplastic materials which can be used are all those which are biologically compatible. Currently, the best biologically compatible thermoplastic material is polyethylene, which is almost exclusively used and is preferred. The polyethylene (PE) used must have the following properties:

linear PE high density of $>0{,}94$ g/cm$^3$, so called HDPE (high density-PE)

high molecular weight ($>50{,}000$ up to $250{,}000$), MFI 190/2,16

($=$Melt Flow Index, 190° C., 1,16 kp) $<0{,}1$ g/10 minutes body compatible; must not contain harmful foreign substances.

Example: Lupolen 5261 Z from BASF AG

Yield stress at 20° C.: 2,3 kp/mm$^2$

E-modulus: 110 kp/mm$^2$ ball-pressure hardness: 4,9 kp/mm$^2$

Other thermoplastic materials may be used, however, provided that they meet the requirement that they can be worked or molded to have the characteristic of being compatible with the body in which they are to be implanted.

It is also possible to make the compatible surface element of carbon, by forming a carbon surface on the carrying element. For example, the carrying element may be a fiber-reinforced thermosetting plastic which has a carbon layer applied thereto as the surface element. The carbon layer can be generated by gas discharge in a hydrocarbon atmosphere, by sputtering, evaporation, or the like, with carbon, or by carbonizing the surface layer of the core element, for example by means of electron beams, or by applying a carbon layer by electron beam deposition. The structure of the carbon layer is that of normal pure graphite or of the pyrolytic isotropic carbon with a density of 1,6 to 2,1 g/cm$^3$, preferably 1,8 g/cm$^3$, and a hardness of DHP 150 to 450.

Carbon has a relatively low coefficient of friction and excellent compatibility with the biological media in the body, and is particularly suited for this application.

The materials in accordance with the present invention have sufficient strength and are compatible with the human body due to their biologically compatible surface element. The modulus of elasticity can be selected by suitable selection of the type of fibers, the percentage of fiber content, and the orientation of the fiber, for example upon manufacture of a mat; thus, the modulus of elasticity can be readily matched to that of bones. Due to this iso-elasticity of bone and implanting structure, differences in reaction of the bone and the implanting element to shock, vibration or jars are avoided. The iso-elasticity, according to current medical knowledge, seems to be one of the conditions for reliable and sure junction of the implanting element in a bone without use of bone cement.

The density of the structure in accordance with the present invention is less than about 2 g/cm$^3$, preferably 1,2 to 1,6 g/cm$^1$; it thus approaches the density of the natural bone, so that the prosthetic bone implants are much lighter in weight than similar bone implants made from previously used materials, or combinations of materials.

The bones have the following properties:
density: ~1,1 g/cm$^3$
tensile strength: ~10 kp/mm$^2$
compressive strength: ~23 kp/mm$^2$
modulus of elasticity (E-modulus) 1400–2100 kp/mm$^2$ The properties of the composite material lie in the following regions:
density: 1,2 to 1,6 g/cm$^3$
flexural strength: 30 to 70 kp/mm$^2$
compressive strength: 20 to 50 kp/mm$^2$
breaking elongation: 0,8 to 2%
ball-indentation hardness on the surface: 12 kp/mm$^2$
E-modulus: 2000 to 10,000 kp/mm$^2$ The core element and, if desired, the surface element as well, is reinforced by means of fibers, particularly carbon fibers or other high-strength, high-modulus materials.

The properties of the materials permit their use as a replacement for bones, particularly for the hip joints. All the portions of the hip joints may be replaced, that is, the femur, the ball of the hip joint, as well as the hip joint socket. Support and connecting elements to be implanted in the body can also be made of the material, for example in the form of braces or plates which may remain in the body for limited or extensive periods of time, for example to set bones which have been fractured.

The thermosetting plastics used as a matrix for the fiber-reinforced core may be of different type. Any kind of resin may be used, but those resins are preferred which are not subject to splitting off extraneous product which may cause difficulty in due time. A further criterion for selection of the thermosetting plastic, particularly if the surface element also is a fiber-reinforced plastic, is the temperature range of processing. The temperature range of softening of the outside thermoplastic, as well as curing of the thermosetting core should overlap. In accordance with the selection criteria, the following core materials are suitable and preferred: epoxide resins, polyester resins, melamine resins, cyanate resins, and imide resins with the following properties:

| E-modulus | | 100 to 700 kp/mm$^2$ |
| flexural strength | at 37° C. | 8 to 15 kp/mm$^2$ |
| breaking elongation | | 1 to 5% | chemically stable with respect to the biological envireonment
no or only little delivery of monomers, stabilizing agents, hardening agents
curing temperature: 130° to 230° C.
decomposition temperature: >250° C.
glas transition temperature: ≳150° C.
Examples for those resins are
(a) "Cyanatharz KU 6573" from Bayer AG, a heat-hardening one-component resin on the basis of a bifunctional aromatic cyanic acid ester with a hardening system consisting of
0,05 wt-% diazabicyclooctane
0,10 wt-% pyrocatechol
0,20 wt-% zincotoate, referred to the weight of the resin;
hardening: 2 hours at 160° C. under a pressure of 40 to 70 bar.
(b) "Epikote DX 210" from Shell AG, an epoxi resin as a solution with "BF$_3$ 400" as a hardener.
hardening: 1 hour at 180° C. under a pressure of >10 bar.

The invention will be described by way of example with reference to the accompanying drawings, wherein.

Figure 1:
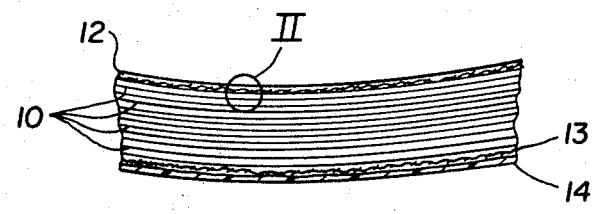
FIG. 1 is a schematic cross-sectional view through a portion of a prosthesis plate, for example, for use as a bone replacement, and illustrating one embodiment of the present invention.
Figure 2:
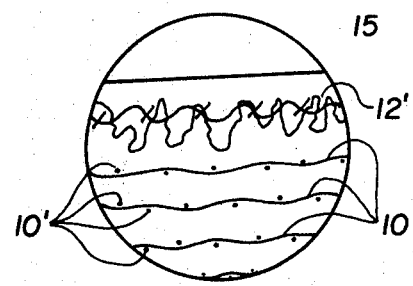
FIG. 2 is a greatly enlarged fragmentary detail view of the portion of the plate of FIG. 1 within the circle II.

A web, which may be a woven mat of fibers 10, or parallel arranged fibers, or a felted open-based mat of fibers is soaked with thermosetting resin. Longitudinal fibers illustrated at 10 (FIG. 1) are crossed by transverse fiber elements 10' (seen in FIG. 2 only). The thermosetting material has been omitted from the showing in the drawings for clarity. The soaked fiber mat forming an inner support structure, is then surrounded with a mat 12. Mat 12 has previously been filled with thermoplastic powder 12' (FIG. 2). Alternatively, a mat 13 (FIG. 1) can be applied on the mat 10 which was soaked in thermosetting material, and a foil 14 of thermoplastic material applied to the outside of mat 13 filled mat 12, or mat 13 and foil 14 form surface structures.

The layers are compressed and, with the thermoplastic foil 14 at the outside, are rolled together or so shaped that the raw general shape of the bone prosthesis to be formed will be apparent. This pre-shaped element is then inserted into a mold, preferably a two-part mold. The overall volume of the pre-formed element is somewhat greater than the volume of the mold when completely closed. The mold, therefore, must have an opening from which excess material can escape when the mold is compressed. The mold with the pre-formed insert is then heated to temperatures from 460° to 200° C. and the mold halves are compressed. The reinforcing mat 12, or 13, respectively, will thus be penetrated from the one side by molten thermosetting resin, and by molten thermoplastic from the other, resulting in an interlocking of the thermoplastic and thermosetting resin which is accentuated by overlapping and undercutting random positioning, as best seen in FIG. 2.

EXAMPLE

A thermoplastic surface, reinforced layer is being formed on a core: A carbon fiber mat is soaked with a cyanate resin solution (Cyanat resin KU 6573 from Bayer AG, Solution in methylethylketone). A further carbon fiber mat is applied on the carbon fiber soaked in resin. The further carbon fiber mat, corresponding to mat 12, or 13, respectively, is either filled with polyethylene powder or a foil 14 of the type Lupolen 52617 from BASFAG is applied. The process will be the same. The layers are compressed—as above explained—with the polyethylene layer towards the outside. The mold, upon compression, is heated to about 160° C., upon which the cyanate resin will penetrate the mat which was not soaked with the thermosetting resin from the one side, and the molten polyethylene will penetrate the mat from the other, causing interlocking of the two plastic materials. After cooling, the cyanate resin has cured; the outer surface of the polyethylene has solidified, resulting in a smooth surface 15 which, after removal from the mold, presents a unitary composite laminar body with a fiber-reinforced polyethylene surface. At those points where excess plastic material was permitted to escape, it may be necessary to apply a polyethylene layer to cover any areas or zones which may not be coated completely with polyethylene.

It might be considered to make a thermosetting core and then coat the thermosetting core with pure polyethylene. It has been found that this does not meet the requirements since the binding force attachment of the pure polyethylene outer coating to the core is not sufficient for the intended use, and the strength and hardness of the polyethylene itself even when reinforced is likewise insufficient for the use intended.

Figure 3:
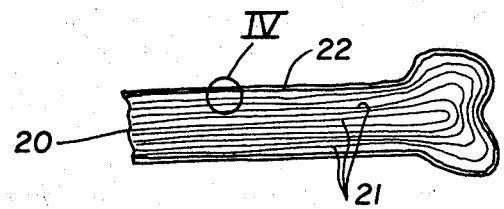
FIG. 3 is a fragmentary cross-sectional view through the end of a bone, and illustrating another embodiment of the present invention.
Figure 4:
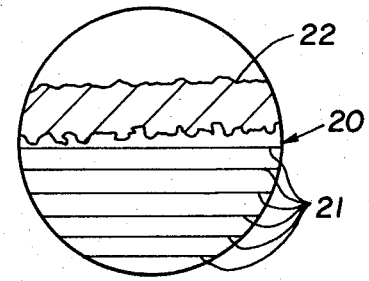
FIG. 4 is a greatly enlarged fragmentary view of the area within the circle IV of FIG. 3.

Embodiment of FIGS. 3 and 4: Elongated carbon fibers 21 are soaked in a thermosetting resin and shaped approximately to have the final shape 20 (FIG. 3) which is desired. The carbon fiber—thermosetting resin combination is cured or set to result in a strong composite body of the desired shape. The then cured body has a surface layer of carbon 22 applied thereto. The surface layer of carbon is generated by exposing the body 20 to a gas discharge in an atmosphere containing hydrocarbons; it may also be generated by evaporation or sputtering carbon on the surface of the body 20, or by carbonizing the surface, for example by exposing the surface to an electron beam. The interface between the surface element 22 and the body 20 again will show, in cross section, an interlocking structure to provide secure attachment between the two elements.

The composite core of made of thermosetting epoxi resin, e.g. DX 210 from Shell AG, reinforced with 60 vol.-% "Morganit II"-carbon fibers aligned in one direction has the following properties:

| | |
|---|---|
| density | 1,58 g/cm$^2$ |
| flexural strength | 145 kp/mm$^2$ |
| compressive strength | 100 kp/mm$^2$ |
| E-modulus | 15000 Kp/mm$^2$ |
| fluxural fatique strength for 10$^7$ cycles | 90 to 115 kp/mm$^2$ |

The material in accordance with the present invention provides a medically acceptable material for prosthetic use which is versatile and has wide applicability. It differs from materials previously used in the medical field, principally metal alloys and aluminum-oxide ceramic materials, by its characteristic of shock absorption and weight. The mechanical strength is sufficient for the purposes intended; sensitivity to impact or jars is much less than in aluminum oxide ceramic materials. The material as described does not have problems associated with corrosion. It is biologically compatible for implantation in the human or animal body due to the surface characteristic or surface layer thereof. The modulus of the elasticity can be matched to the range of that of natural bones, in contrast to previously used materials. The density or unit weight of the material of less than 2 g/cm$^3$ is similar to that of natural bone and is substantially less than that of the previously used materials. Thus, any implanted elements made of the material have a much lesser weight than metal alloys or oxide ceramic materials heretofore proposed.

Various changes and modifications may be made within the scope of the inventive concept.

We claim:

1. Method to make a bone replacement prosthetic structure or appliance of a biologically compatible material suitable as a bone replacement prosthetic implant including a core element made of a fiber-reinformed thermosetting material; and a surface element made of a biologically compatible fiber reinforced thermoplastic material completely surrounding said core element and internally interlocked with the core element comprising steps of providing an inner support structure of at least one material selected from the group consisting of:

elongated essentially parallel positioned fibers, woven fiber fabric, fiber mats, matted fibers and felted fibers;

soaking the support structure in a thermo-setting resin;

surrounding said soaked inner support structure with a surface structure comprising a biologically compatible thermoplastic resin, at least a portion of the thermoplastic resin being at the side remote from the thermosetting resin soaked support structure to form a sub-assembly, said thermosetting resin being a resin that will cure at a temperature which overlaps in the temperature range of from 160° C. to 200° C. with the temperature range of softening of said thermoplastic resin;

introducing said sub-assembly into a mold having the desired shape of the prosthetic structure or appliance;

simultaneously heating to a temperature of from 160° C. to 200° C. at which said thermosetting resin cures and said thermoplastic resin softens and compressing the mold to compress the sub-assembly and cure the thermosetting resin and thereby form said core element and mold the thermoplastic resin and thereby causing the outer thermoplastic structure to interlock with the inner support structure and forming the surface structure with an outer surface consisting essentially only of thermoplastic resin; and removing the mold after cooling to a temperature at which the outer surface of the thermoplastic resin has solidified.

2. Method according to claim 1 wherein said biologically compatible theremoplastic resin comprises polyethylene.

3. Method according to claim 2 wherein said polyethylene is a linear high density polyethylene.

4. Method according to claim 1, including the step of surrounding said soaked support structure with a reinforcing material comprising at least one material selected from the group consisting of: elongated fibers; woven fiber fabric; fiber mats; matter fibers and felted fibers;

and applying said biologically compatible thermoplastic resin to said surface structure at least at the outside, with respect to the core support structure.

5. Method according to claim 4, wherein the step of applying said biologically compatible thermoplastic resin comprises applying said thermoplastic resin material in powder form both at the inside as well as at the outside of said reinforcing material.

6. Method according to claim 4, wherein the step of applying said biologically compatible thermoplastic resin comprises applying said theremoplastic resin material in sheet form at the outside of said reinforcing material.

7. Method according to claim 1 wherein the material of the inner support structure comprises carbon fibers.

8. Method according to claim 4 wherein the material of said reinforcing material comprises carbon fibers.

9. Method according to claim 8 wherein the material of the inner support structure comprises carbon fibers.

10. Method according to claim 9 wherein said thermoplastic resin is a linear high density polyethylene.

* * * * *

UNITED STATES PATENT AND TRADEMARK OFFICE
CERTIFICATE OF CORRECTION

PATENT NO. : 4,268,468
DATED : May 19, 1981
INVENTOR(S) : Friedrich J. ESPER et al It is certified that error appears in the above—identified patent and that said Letters Patent is hereby corrected as shown below:

Title Page, left column, under the heading "FOREIGN APPLICATION PRIORITY DATA", the line under said heading should read:

--Jan. 30, 1976 [DE]   Fed. Rep. of Germany.....2603456--.

Signed and Sealed this

Twenty-third Day of March 1982

[SEAL]

Attest:

GERALD J. MOSSINGHOFF

Attesting Officer

Commissioner of Patents and Trademarks